(12) United States Patent
Ko

(10) Patent No.: US 8,323,582 B2
(45) Date of Patent: Dec. 4, 2012

(54) QUANTITATIVE LIQUID INJECTION DEVICE OF PLASMA STERILIZER

(75) Inventor: Jung Suek Ko, Seoul (KR)

(73) Assignee: Human Meditek Co., Ltd., Seoul (KR)

( * ) Notice: Subject to any disclaimer, the term of this patent is extended or adjusted under 35 U.S.C. 154(b) by 605 days.

(21) Appl. No.: 12/528,410

(22) PCT Filed: Feb. 21, 2008

(86) PCT No.: PCT/KR2008/001015
§ 371 (c)(1),
(2), (4) Date: Nov. 2, 2009

(87) PCT Pub. No.: WO2008/102993
PCT Pub. Date: Aug. 28, 2008

(65) Prior Publication Data
US 2010/0099173 A1   Apr. 22, 2010

(30) Foreign Application Priority Data
Feb. 23, 2007   (KR) .................. 10-2007-0018586

(51) Int. Cl.
*A61L 2/00* (2006.01)
*G01F 11/04* (2006.01)
*G01F 11/20* (2006.01)
*B65D 88/54* (2006.01)

(52) U.S. Cl. ........ 422/300; 422/563; 422/297; 422/298; 422/299; 422/305; 222/309; 222/319; 222/249; 222/340; 222/409; 222/525; 222/526; 222/413; 222/333

(58) Field of Classification Search .................. 422/563, 422/297–300, 305; 73/1.36, 239; 216/58; 222/309, 319, 249, 340, 409, 525–526, 413, 222/333
See application file for complete search history.

(56) References Cited

U.S. PATENT DOCUMENTS

| | | | |
|---|---|---|---|
| 4,756,882 A | 7/1988 | Jacobs et al. | |
| 7,048,157 B2 * | 5/2006 | Marchadour | ................. 222/413 |
| 7,101,518 B1 | 9/2006 | Ko | |

FOREIGN PATENT DOCUMENTS

| | | |
|---|---|---|
| DE | 3902116 C1 | 10/1990 |
| JP | 61234926 A | 10/1986 |

(Continued)

OTHER PUBLICATIONS

PCT International Search Report for PCT/KR2008/001015.

*Primary Examiner* — Jill Warden
*Assistant Examiner* — Monzer Chorbaji
(74) *Attorney, Agent, or Firm* — The Webb Law Firm

(57) ABSTRACT

Disclosed herein is a device for quantitatively supplying a liquid in a plasma sterilization system. The device includes a quantitative cylinder, a quantitative piston and a quantitative basket. The quantitative cylinder includes a quantitative inlet pipe, which is configured such that the outlet of a liquid container is inserted thereinto, and a liquid in the liquid container is vertically supplied to the quantitative cylinder, and a quantitative outlet pipe, which is configured such that the liquid is vertically drained from the quantitative cylinder. The quantitative piston is configured to rectilinearly reciprocate in the quantitative cylinder, and is provided with a quantitative transfer depression, which is formed in the leading end thereof to a predetermined depth. The quantitative basket is configured to quantitatively receive the liquid according to the rectilinear reciprocation of the quantitative piston.

7 Claims, 3 Drawing Sheets

FOREIGN PATENT DOCUMENTS

| | | | |
|---|---|---|---|
| JP | 1-92237 | * | 6/1989 |
| JP | 192237 U | | 6/1989 |
| JP | 2002-360672 | | 12/2002 |
| JP | 2006-204889 | | 8/2006 |
| KR | 97010057 B1 | | 6/1997 |
| KR | 1020020084213 A | | 11/2002 |
| WO | 0170281 A1 | | 9/2001 |
| WO | 2007018742 A2 | | 2/2007 |

* cited by examiner

QUANTITATIVE LIQUID INJECTION DEVICE OF PLASMA STERILIZER

TECHNICAL FIELD

The present invention relates to a device for quantitatively supplying a liquid in a plasma sterilization system and, more particularly, to a device for quantitatively supplying a liquid in a plasma sterilization system using a hydrogen peroxide solution, which, when sterilization is performed to kill germs present on the surface of a target article, such as medical equipment, which is desired to be sterilized, using both hydrogen peroxide vapor, which is generated by supplying a liquid hydrogen peroxide solution and evaporating and diffusing the supplied solution in a plasma sterilization system, and plasma, enables the automatic supply of a quantitative liquid sterilizing solution, that is, a very small amount of hydrogen peroxide solution.

BACKGROUND ART

Conventionally, various methods have been used in order to sterilize disposable or reusable medical equipment. Of such methods, methods of using steam or dry heat have been widely used, but are disadvantageous in that they cannot be used when target articles to be sterilized are heat- or steam-sensitive.

Also, there is a method of using ethylene oxide (EtO) gas. However, this method is disadvantageous in that, because toxic residues may remain on sterilized target articles and cause serious harm to patients who use the sterilized target articles, it is necessary to perform an additional process of removing such toxic residues remaining on the sterilized target articles, which requires excessive expenses and time.

As one method for solving this disadvantage, a method of performing sterilization in such a way as to bring a target sterilization article, which will be sterilized, into contact with hydrogen peroxide vapor in advance and to generate an active species from hydrogen peroxide, and decomposing and removing the hydrogen peroxide remaining on the target article using plasma and non-toxic products was proposed in Korean Pat. No. 10-0132233, entitled "Hydrogen Peroxide Plasma Sterilization System."

In the above-described low-temperature plasma sterilization system, a device for supplying hydrogen peroxide solution employs a capsule-type cassette system in which a predetermined amount of hydrogen peroxide solution is injected into a capsule. A cassette is transferred to an injector valve assembly and is moved to an evaporator due to the pressure difference that is caused by the vacuum in the sterilization chamber, and thus the liquid contained in the capsule is evaporated into vapor and is then supplied to a sterilization reactor.

However, the above-described method is disadvantageous in that, after a sterilization process is performed ten times using one capsule-type cassette having ten capsules (for example, one capsule is used for a single sterilization process), the existing cassette must be replaced with a new cassette into which ten capsules are loaded. Furthermore, the above-described device for quantitatively supplying a very small amount of liquid is disadvantageous in that the structure thereof is very complicated and the price thereof is high.

Accordingly, in order to solve the above-described problems, a device for supplying a liquid for plasma generation, which can eliminate the inconvenience of exchanging a cassette, can reduce the manufacturing cost because the structure thereof is simple, and can quantitatively and automatically supply a very small amount of hydrogen peroxide solution for plasma generation, was previously submitted by the present applicant, and was registered (Korean Pat. No. 10-396195).

The above-described device for supplying a liquid for plasma generation is configured such that the hydrogen peroxide solution is quantitatively supplied to a reaction container while a piston reciprocates in response to the operation of a motor. However, the above-described device is also disadvantageous in that the structure thereof is complicated and in that the liquid is not supplied in a quantitative and accurate manner.

Furthermore, as shown in FIGS. 1 and 2, a device 10 for supplying a liquid for plasma generation, which is configured such that a hydrogen peroxide solution, which is drained from a hydrogen peroxide solution container, is collected in a separate tank 12, the collected hydrogen peroxide solution is drained from the tank 12 to a separate basket 20 using a solenoid valve 14, and the hydrogen peroxide solution collected in the basket 20 is quantitatively supplied to a reaction container using a solenoid valve 22, was proposed.

However, in the above-described construction, the hydrogen peroxide solution is quantitatively supplied to the basket using the solenoid valves, so that, when an electrical problem occurs, there is the concern that the hydrogen peroxide solution may not be quantitatively supplied to the basket.

Furthermore, there are problems in that a separate measurement sensor for detecting whether the hydrogen peroxide solution is quantitatively supplied to the basket must be provided, and in that the construction of the device becomes complicated because the opening and closing of the solenoid valves must be controlled in response to the detecting operation of the measurement sensor.

DISCLOSURE

Technical Problem

Accordingly, the present invention has been made keeping in mind the above problems occurring in the prior art, and the present invention is directed to provide a device for quantitatively supplying a liquid in a plasma sterilization system using a hydrogen peroxide solution, which, when sterilization is performed to kill germs present on the surface of a target article, such as medical equipment, which is desired to be sterilized, using both hydrogen peroxide vapor and plasma, enables the automatic supply of a quantitative liquid sterilizing solution, that is, a very small amount of hydrogen peroxide solution, and which, in addition, has a simple structure.

Furthermore, the present invention is directed to provide a device for quantitatively supplying a liquid in a plasma sterilization system, which enables a hydrogen peroxide solution to be quantitatively supplied using a simple construction and principle, based on a quantitative cylinder and a quantitative piston, and in which the structure thereof is greatly simplified because it is not necessary to mount a separate measurement sensor to a quantitative basket.

Furthermore, the present invention is directed to provide a device for quantitatively supplying a liquid in a plasma sterilization system, which, in the case where the use period of the liquid in the quantitative cylinder has elapsed, enables the liquid to be easily removed using a drain cylinder, thus facilitating the maintenance thereof.

Technical Solution

In order to accomplish the above objects, the present invention provides a device for quantitatively supplying a liquid in a plasma sterilization system, including: a quantitative cylinder including a quantitative inlet pipe, which is configured such that the outlet of a liquid container is inserted thereinto, and a liquid in the liquid container is vertically supplied to the quantitative cylinder, and a quantitative outlet pipe, which is configured such that the liquid is vertically drained from the quantitative cylinder; a quantitative piston configured to rectilinearly reciprocate in the quantitative cylinder, and provided with a quantitative transfer depression, which is formed in the leading end thereof to a predetermined depth; and a quantitative basket configured to quantitatively receive the liquid according to the rectilinear reciprocation of the quantitative piston.

In this case, it is preferred that the quantitative transfer depression of the quantitative piston be located on the same line as the quantitative outlet pipe of the quantitative cylinder when the quantitative piston is located at a bottom dead center, and that it is located on the same line as the quantitative inlet pipe of the quantitative cylinder when the quantitative piston is located at a top dead center.

Furthermore, it is preferred that the device further include a bypass flow path for bypassing air present in the quantitative cylinder, when the quantitative piston is moved to a bottom dead center, the bypass flow path being formed in the quantitative cylinder.

Furthermore, it is preferred that the outlet portion of the bypass flow path be located on the same line as the quantitative transfer depression of the quantitative piston when the quantitative piston reaches the bottom dead center.

Meanwhile, it is preferred that the device further include a drain cylinder for removing the liquid when the use period of the liquid in the quantitative cylinder has elapsed.

It is preferred that the drain cylinder include a drain cylinder body comprising a drain inlet pipe, which is connected with a space inside the quantitative cylinder, and a drain outlet pipe, which is configured to vertically drain the liquid; a drain piston configured to rectilinearly reciprocate in the drain cylinder, and provided with a drain transfer depression, which is formed in the leading end thereof to a predetermined depth; and a drain basket configured to receive a liquid, which will be removed, according to the rectilinear reciprocation of the drain piston.

In this case, it is preferred that a bypass flow path be formed in the leading end of the drain piston.

Furthermore, it is preferred that the drain inlet pipe and the drain outlet pipe be connected to each other via the drain transfer depression when the drain piston is moved to a bottom dead center.

Furthermore, it is preferred that the drain inlet pipe and the drain outlet pipe be closed by the drain piston when the drain piston is moved to a top dead center.

Advantageous Effects

As described above, in the device for quantitatively supplying a liquid in a plasma sterilization system, the structure becomes simplified using the quantitative cylinder and the quantitative piston and, thus, the manufacturing cost thereof is reduced. Furthermore, a liquid, that is, hydrogen peroxide solution, can be quantitatively injected into the quantitative basket according to the number of rectilinear reciprocations of the piston.

Furthermore, the hydrogen peroxide solution can be quantitatively supplied to the quantitative basket according to the number of rectilinear reciprocations of the quantitative piston, and thus it is not necessary to mount a separate measurement sensor to the quantitative basket.

Furthermore, in the case where the use period of the hydrogen peroxide solution remaining in the quantitative cylinder has elapsed, the hydrogen peroxide solution can be drained into the drain basket using the drain cylinder and the drain piston, and thus the maintenance of the device is facilitated.

DESCRIPTION OF REFERENCE NUMERALS OF PRINCIPLE ELEMENTS

Figure 1:
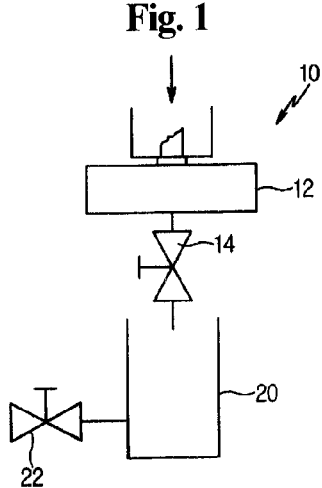
FIGS. 1 and 2 are diagrams showing the construction of a conventional device for quantitatively supplying a liquid in a plasma sterilization system.
Figure 2:
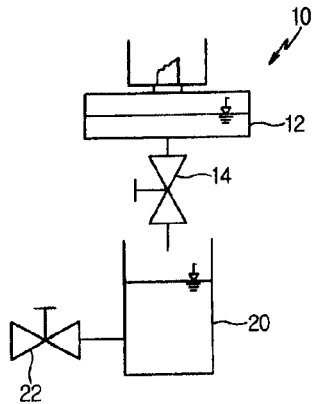

100: quantitative liquid injection device
101: quantitative cylinder body
102: quantitative inlet pipe
104: bypass flow path
105: quantitative outlet pipe
106: quantitative piston
107: quantitative transfer depression
110: quantitative basket
108: drain piston
160: drain transfer depression
162: drain outlet pipe
163: drain inlet pipe
170: drain cylinder body
171: drain basket

BEST MODE

A preferred embodiment of the present invention is described in detail with reference to the accompanying drawings below.

Figure 3:
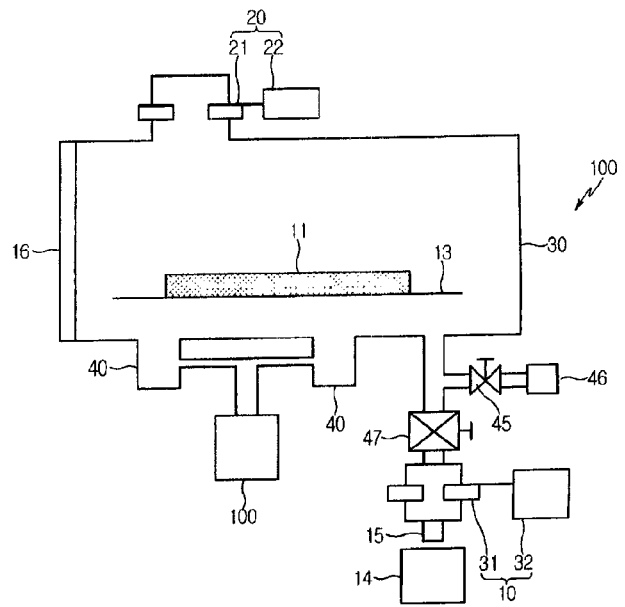
FIG. 3 is a diagram showing the construction of a plasma sterilization system to which a device for quantitatively supplying a liquid according to the present invention is applied.

FIG. 3 is a diagram showing the construction of a plasma sterilization system to which a device for quantitatively supplying a liquid according to the present invention is applied. Here, the system is used to sterilize a target article using gaseous hydrogen peroxide vapor and plasma.

In particular, the present invention uses a sterilization solution, that is, a hydrogen peroxide solution, in order to kill germs present on the surface of a target article, such as medical equipment, which is desired to be sterilized, and includes a process of performing sterilization using both hydrogen peroxide vapor and a reaction active material, which is generated during the generation of plasma, and performing pretreatment using gaseous hydrogen peroxide prior to the generation of plasma.

As shown in the drawing, the reaction container 30 of the present invention is a chamber that is configured such that a target article 11, such as medical equipment or a surgical tool, which is desired to be sterilized, can be placed therein in the state in which the target article 11 is wrapped using a packaging material. A tray 13, which is configured such that the target article 11 can be placed thereon, is installed in the reaction container 30. In order to create a vacuum state in the reaction container 30 by evacuating the gases in the reaction container 30, a vacuum pump 14 is installed below the reaction container 30 and is connected to a discharge line 15. Furthermore, a door 16 is installed in one side of the reaction container 30.

A plasma generator 20 is provided outside the reaction container 30. This plasma generator 20 includes a plasma chamber 21, in which two electrodes are mounted opposite each other. A high power supply source 22, having a frequency for generating optimal plasma, is electrically connected to the electrodes of the plasma chamber 21.

A plasma processor 10 is provided in the discharge line 15 in order for the gases in the reaction container 30 to pass through the plasma. This plasma processor 10 includes a plasma chamber 31 and a high power supply source 32.

The device 100 for quantitatively supplying a liquid is connected to the outer portion of the reaction container 30 so that a hydrogen peroxide solution, which is a disinfectant, can be supplied to evaporation ports 40. When the liquid hydrogen peroxide solution, which is quantitatively controlled, is supplied to the insides of the evaporation ports 40, the evaporation ports 40 generate hydrogen peroxide vapor while evaporating and diffusing the supplied hydrogen peroxide solution.

In the drawing, reference numeral 47 indicates a pressure control valve. The pressure control valve is provided in the discharge line 15 in order to control the vacuum conditions in the reaction container 30.

Furthermore, a pressure removal valve 45 for removing the vacuum conditions in the reaction container 30 is provided in the reaction container 30. A filter 46 for removing foreign materials from the external air that enters the pressure removal valve 45 is provided.

Figure 4:
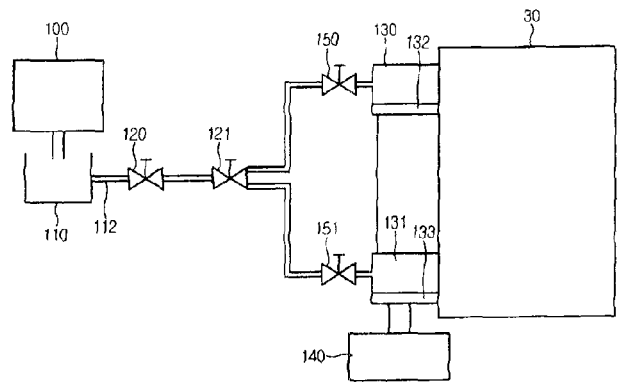
FIG. 4 is a diagram illustrating the operation of the device for quantitatively supplying a liquid in a plasma sterilization system according to the present invention.

Meanwhile, FIG. 4 is a diagram illustrating the operation of the device for quantitatively supplying a liquid, which is the principal part of the present invention. The device for quantitatively supplying a liquid is used such that a liquid for plasma generation in an automatic liquid supply device is evaporated in a first evaporator 130 and a second evaporator 131 via a first exhaust supply pipe 112 and a second exhaust supply pipe 113, and is then supplied to the reaction container 30. The automatic liquid supply device automatically supplies a very small amount of liquid for plasma generation to the first exhaust supply pipe 112 using a quantitative cylinder body 101 and a quantitative piston 106, in response to the rotation of a motor (not shown).

In this case, the very small amount of liquid for plasma generation, which is supplied by the automatic liquid supply device, that the hydrogen peroxide solution, is collected in a quantitative basket 110, and is then automatically supplied to the second exhaust supply pipe 113 by a first solenoid valve 120 and a 3-Way valve 121, which are mounted to the first exhaust supply pipe 112.

The hydrogen peroxide solution, which is supplied to the second exhaust supply pipe 113, is supplied to a first evaporator 130 and a second evaporator 131 via a second solenoid valve 150 and a third solenoid valve 151, is evaporated by the first heater 132 of the first evaporator 130 and the second heater 133 of the second evaporator 131, and is then supplied to the reaction container 30.

The first and second heaters 132 and 133 are respectively mounted to the first and second evaporators 130 and the second evaporator 131 in order to evaporate a liquid. The first and second heaters 132 and 133 control temperature using respective temperature controllers, which are electrically connected thereto.

The device 100 for quantitatively supplying a liquid includes a quantitative cylinder and a drain cylinder. The space 103 inside the quantitative cylinder and the space 109 inside the drain cylinder are connected with a quantitative inlet pipe 102 and a drain inlet pipe 163, respectively.

Figure 5:
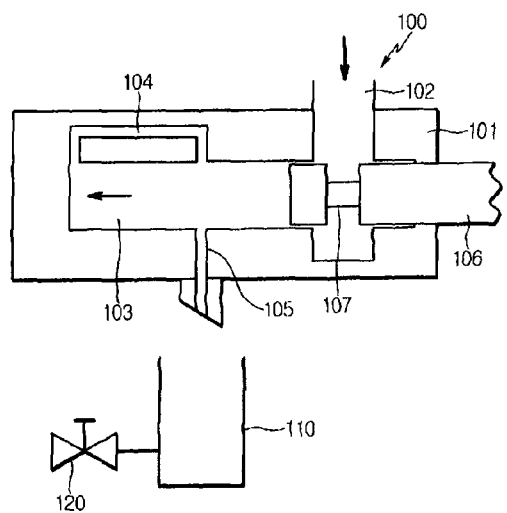
FIGS. 5 and 6 are diagrams showing, in detail, the structure of a quantitative cylinder in the device for quantitatively supplying a liquid, shown in FIG. 4.
Figure 6:
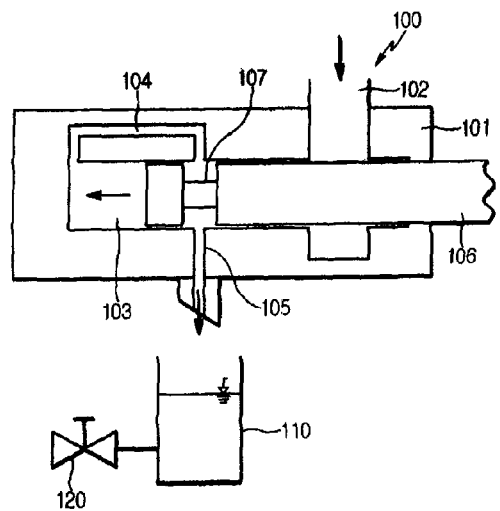

In the device 100 for quantitatively supplying a liquid, the quantitative cylinder, as shown in FIGS. 5 and 6, includes an inlet pipe 102, which is mounted to a liquid container, that is, to a hydrogen peroxide solution container, to receive a hydrogen peroxide solution from the container, a quantitative cylinder body 101, which is provided with an outlet pipe 105 for draining a predetermined amount of hydrogen peroxide solution into the quantitative basket 110, and a quantitative piston 106, which is configured to drain a predetermined amount of hydrogen peroxide solution, which is received from the inlet pipe 102, into the outlet pipe 105 while rectilinearly reciprocating in the space 103 inside the quantitative cylinder.

A quantitative transfer depression 107 is formed in a portion of the leading end of the quantitative piston 106. This quantitative transfer depression 107 is located on the same line as the outlet pipe 105 of the quantitative cylinder when the quantitative piston 106 is located at a bottom dead center, and is located on the same line as the inlet pipe 102 of the quantitative cylinder when the quantitative piston 106 is located at a top dead center.

Meanwhile, a bypass flow path 104 is formed in the quantitative cylinder. The bypass flow path 104 is configured such that compressed air passes therethrough and is sprayed into the quantitative transfer depression 107 in the quantitative piston 106 when the quantitative piston 106 is moved to the bottom dead center. Accordingly, the bypass flow path 104 functions to easily drain the hydrogen peroxide solution into the quantitative basket 110 via the outlet pipe 105 using the quantitative transfer depression 107 in the quantitative piston 106.

The operation of the quantitative cylinder of the device 100 for quantitatively supplying a liquid, which is constructed as described above, is described in detail below.

First, when the quantitative piston 106 is located at the top dead center, that is, at the location at which it is moved backwards in the quantitative cylinder, in the state in which the hydrogen peroxide solution container (not shown), the lid of which is opened, is inserted into the inlet pipe 102 of the quantitative cylinder, as shown in FIG. 5, the hydrogen peroxide solution in the container is vertically charged in the inlet pipe 102 of the quantitative cylinder, including the quantitative transfer depression 107 of the quantitative piston 106, to predetermined height.

In this state, when a driving signal is applied to the motor, the quantitative piston 106 is moved toward the bottom dead center, that is, is moved forward in the quantitative cylinder. In this case, a predetermined amount of hydrogen peroxide solution, which is present in the quantitative transfer depression 107 in the quantitative piston 106, is moved along the quantitative piston 106, as shown in FIG. 6.

When the quantitative piston 106 is moved forwards, the air Present in the space 103 inside the quantitative cylinder passes through the bypass flow path 104 due to pressure. The air, which passes through the bypass flow path 104, is send to the quantitative transfer depression 107 in the state in which the quantitative piston 106 is moved forwards.

Furthermore, when the quantitative piston 106 reaches the bottom dead center, the quantitative transfer depression 107 is located on the same line as the outlet pipe 105 of the quantitative cylinder. Accordingly, the predetermined amount of hydrogen peroxide solution, which is located in the quantitative transfer depression 107, is vertically moved into the quantitative basket 110 via the outlet pipe 105 by the air that passes through the bypass flow path 104.

After the predetermined amount of hydrogen peroxide solution has been supplied to the quantitative basket 110, the quantitative piston 106 is moved to the top dead center and, subsequently, is moved to the bottom dead center again. This process is repeated, and thus the predetermined amount of hydrogen peroxide solution is continuously and quantitatively supplied to the quantitative basket 110.

The hydrogen peroxide solution, which is quantitatively supplied to the quantitative basket 110, is supplied to the evaporators via the solenoid valve 120 and, subsequently, is supplied to the reaction container.

As described above, the amount of hydrogen peroxide solution supplied to the quantitative basket 110 is adjusted according to the number of reciprocations of the quantitative piston 106. Accordingly, the amount of hydrogen peroxide solution that is supplied can be accurately measured without requiring that a separate sensor be mounted to the quantitative basket 110.

Figure 7:
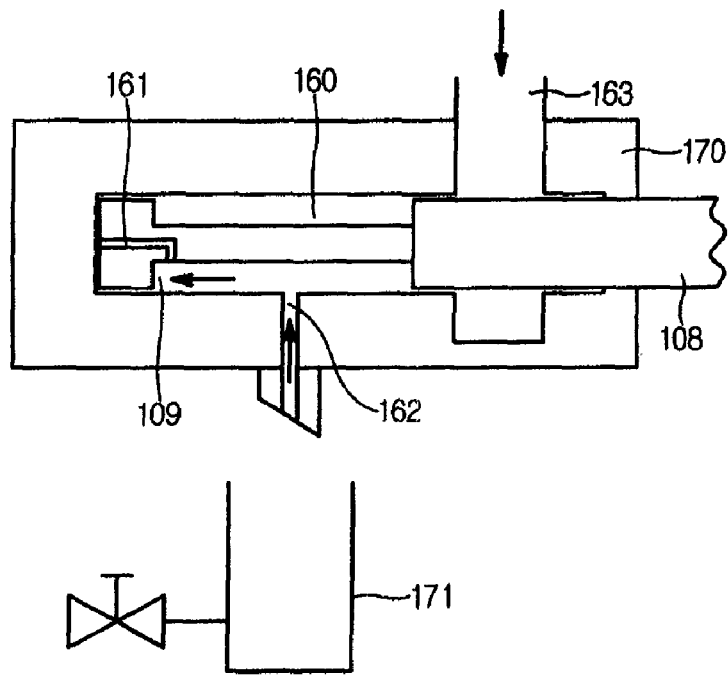
FIGS. 7 and 8 are diagrams showing, in detail, the structure of a drain cylinder in the device for quantitatively supplying a liquid.
Figure 8:
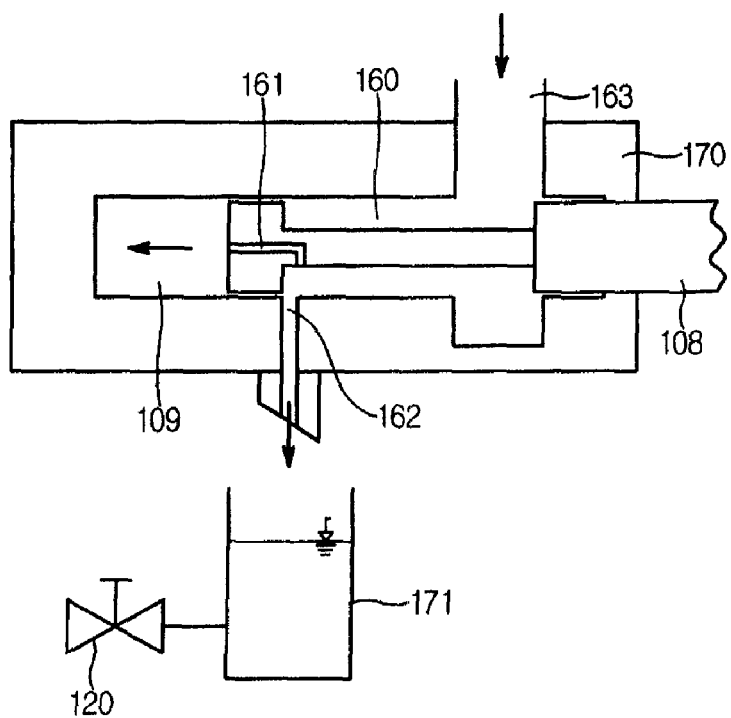

In the device 100 for quantitatively supplying a liquid, the drain cylinder, as shown in FIGS. 7 and 8, includes a drain inlet pipe 163, which is configured to receive a hydrogen peroxide solution from the quantitative cylinder, and a drain piston 108, which is configured to drain a hydrogen peroxide solution, which is received from the drain inlet pipe 163 and the use period of which has elapsed, into a drain basket 171 via a drain outlet pipe 162 while rectilinearly reciprocating in the space 109 inside the drain cylinder.

A drain transfer depression 160 having a great depth is formed in the leading end of the drain piston 108. This drain transfer depression 160 closes the drain inlet pipe 163 when the drain piston 108 is located at a bottom dead center, as shown in FIG. 7, and forms a connection pipe between the drain inlet pipe 163 and the drain outlet pipe 162 when the drain piston 108 is located at a top dead center, as shown in FIG. 8.

Meanwhile, a bypass flow path 161 is formed in the drain piston 108. This bypass flow path 161 is configured such that compressed air passes therethrough and is sprayed to the drain transfer depression 160 in the drain piston 108 when the drain piston 108 is moved to the bottom dead center. Accordingly, the bypass flow path 161 functions to easily drain a hydrogen peroxide solution, the use period of which has elapsed, into the drain basket 171 via the drain outlet pipe 162 using the drain transfer depression 160 in the drain piston 108.

The operation of the drain cylinder of the device 100 for quantitatively supplying a liquid, which is constructed as described above, is described in detail below.

First, the drain piston 108 is located at the bottom dead center, that is, at a location at which it is moved forwards in the drain cylinder in the state in which the hydrogen peroxide solution in the quantitative cylinder, the use period of which has elapsed, flows into the drain inlet pipe 163 of the drain cylinder, as shown in FIG. 7, and the drain transfer depression 160 does not form any connection pipe between the drain inlet pipe 163 and the drain outlet pipe 162, and thus the hydrogen peroxide solution is fully charged in both the drain inlet pipe 163 and the quantitative cylinder body 101.

In this state, when a driving signal is applied to the motor, the drain piston 108 is moved toward the top dead center, that is, is moved backwards in the drain cylinder. In this case, the drain transfer depression 160 of the drain piston 108 forms the connection pipe between the drain inlet pipe 163 and the drain outlet pipe 162, as shown in FIG. 8, and thus the hydrogen peroxide, the use period of which has elapsed, is drained into the drain basket 171.

In this case, the air present in the space 109 inside the drain cylinder passes through the bypass flow path 161 according to the forward or backward movement of the drain piston 108, and thus constant pressure is maintained in the space 109 inside the drain cylinder.

The invention claimed is:

1. A device for quantitatively supplying a liquid in a plasma sterilization system, comprising:
a quantitative cylinder comprising a quantitative inlet pipe, which is configured such that an outlet of a liquid container is inserted theretinto, and a liquid in the liquid container is vertically supplied to the quantitative cylinder, and a quantitative outlet pipe, which is configured such that the liquid is vertically drained from the quantitative cylinder;
a quantitative piston configured to rectilinearly reciprocate in the quantitative cylinder, and provided with a quantitative transfer depression, which is formed in a leading end thereof to a predetermined depth;
a quantitative basket configured to quantitatively receive the liquid according to rectilinear reciprocation of the quantitative piston, wherein the quantitative transfer depression of the quantitative piston is located on a line identical to the quantitative outlet pipe of the quantitative cylinder when the quantitative piston is located at a bottom dead center, and is located on a line identical to the quantitative inlet pipe of the quantitative cylinder when the quantitative piston is located at a top dead center; and a drain cylinder for removing the liquid when a use period of the liquid in the quantitative cylinder has elapsed, and wherein the drain cylinder further comprises: a drain cylinder body comprising a drain inlet pipe, which is connected with a space inside the quantitative cylinder, and a drain outlet pipe, which is configured to vertically drain the liquid; a drain piston configured to rectilinearly reciprocate in the drain cylinder, and provided with a drain transfer depression, which is formed in a leading end thereof to a predetermined depth; and a drain basket configured to receive a liquid, which will be removed according to rectilinear reciprocation of the drain piston.

2. The device according to claim 1, further comprising a bypass flow path for bypassing air present in the quantitative cylinder, when the quantitative piston is moved to a bottom dead center, the bypass flow path being formed in the quantitative cylinder.

3. The device according to claim 2, wherein an outlet portion of the bypass flow path is located on a line identical to the quantitative transfer depression of the quantitative piston when the quantitative piston reaches the bottom dead center.

4. The device according to claim 1, wherein a bypass flow path is formed in a leading end of the drain piston.

5. The device according to claim 1, wherein the drain inlet pipe and the drain outlet pipe are connected to each other via the drain transfer depression when the drain piston is moved to a bottom dead center.

6. The device according to claim 5, wherein the drain inlet pipe and the drain outlet pipe are closed by the drain piston when the drain piston is moved to a top dead center.

7. The device according to claim 1, wherein the drain inlet pipe and the drain outlet pipe are closed by the drain piston when the drain piston is moved to a top dead center.

* * * * *